（12) United States Patent
Rainer et al.

(10) Patent No.: US 6,195,160 B1
(45) Date of Patent: Feb. 27, 2001

(54) ILLUMINATING MEANS FOR REFRACTOMETER

(75) Inventors: Michael D. Rainer; Aaron J. Becker, both of Chagrin Falls, OH (US)

(73) Assignee: The Mercury Iron & Steel Co., Cleveland, OH (US)

( * ) Notice: Subject to any disclaimer, the term of this patent is extended or adjusted under 35 U.S.C. 154(b) by 0 days.

(21) Appl. No.: 09/418,071

(22) Filed: Oct. 14, 1999

Related U.S. Application Data

(60) Provisional application No. 60/104,193, filed on Oct. 14, 1998.

(51) Int. Cl.$^7$ .................................................. G01N 21/41
(52) U.S. Cl. ............................................ 356/135; 356/136
(58) Field of Search ................................ 356/128, 135, 356/136, 137

(56) References Cited

U.S. PATENT DOCUMENTS

| 2,601,128 | 6/1952 | Rosenthal et al. | |
| 4,243,321 | 1/1981 | Okuda et al. | 356/135 |
| 4,650,323 | 3/1987 | Nakagawa | 356/135 |
| 4,890,916 | 1/1990 | Rainer | 356/135 |
| 5,859,696 | * 1/1999 | Nicholas et al. | 356/135 |
| 5,969,808 | * 10/1999 | Cotton et al. | 356/135 |

* cited by examiner

Primary Examiner—F. L Evans
(74) Attorney, Agent, or Firm—Watts, Hoffmann, Fisher & Heinke, Co.

(57) ABSTRACT

An illuminator for use in a refractometer having a body housing, a sample cover assembly, a prism assembly and measuring assembly for measuring the composition and density of a substance. The illuminator includes a light source, a power source for operating the light source and an operating means for selectively activating the light source. The illuminator is located in the refractometer housing such that the light source is in a position on or about the prism assembly to illuminate a fluid substance to be measured. Light from the light source is introduced at a grazing incidence to a measuring surface of the prism. Phosphorescent material in the sample cover provides reticle illumination.

14 Claims, 4 Drawing Sheets

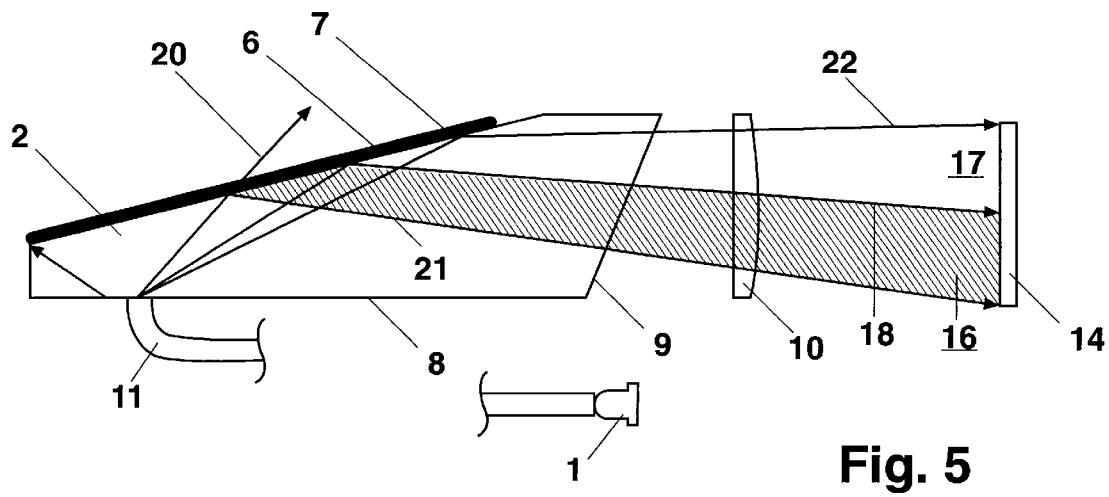
Fig. 5
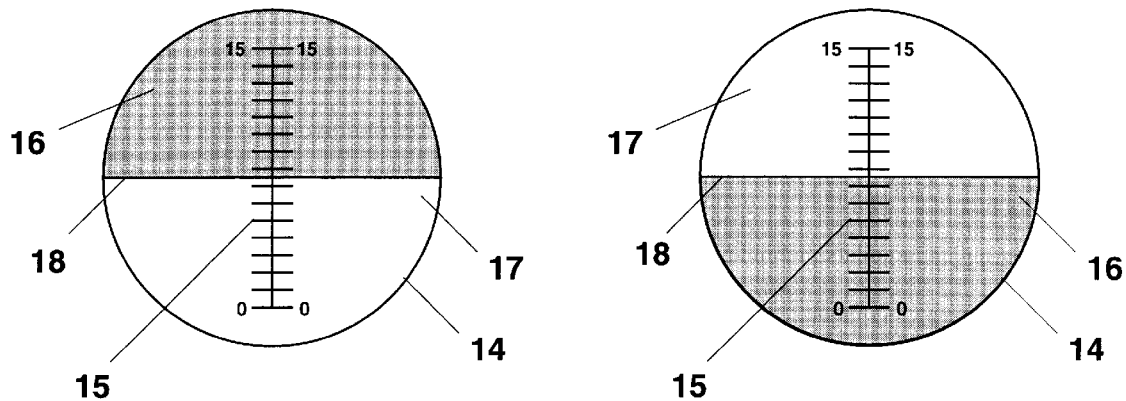
Fig. 6A
Prior Art
Fig. 6B

ILLUMINATING MEANS FOR REFRACTOMETER

This application claims the benefit under 35 U.S.C. §119(e) of U.S. provisional application Ser. No. 60/104,193 entitled "ILLUMINATING MEANS FOR REFRACTOMETER", filed Oct. 14, 1998.

TECHNICAL FIELD

This device relates generally to critical angle type hand-held refractometers used for testing the physical properties of unknown liquids and more specifically to refractometers with illuminating means.

BACKGROUND OF THE INVENTION

A refractometer is a device for measuring the refractive index of a liquid substance. Refractometers are commonly used in industry where it is advantageous to know the specific relationship between two chemical species in a binary mixture.

When light passes from one medium (n1) into another (n2) with a refractive index different than the first, the relationship between the angle of incidence and the angle of refraction can be represented by Snell's Law:

Refractive index($n1$)·Sin(Angle of Incidence)=Refractive index($n2$)·Sin(Angle of refraction)

When the angle of incidence exceeds a certain angle, all light ceases to be refracted and is instead total internally reflected at the boundary between the two mediums. This angle of incidence is the "critical angle" and is a well documented scientific principle.

Critical angle is defined as:

$$\phi_C = \sin^{-1}(n2/n1)$$

Where n1 is the refractive index of the first, light incident, medium and n2 is the refractive index of the second medium.

Known critical angle type hand-held refractometers typically incorporate a series of optical elements arranged to measure the refractive index of a solution under test. These optical elements may consist of a primary critical-angle prism, a transparent sample cover, an objective lens, a reticle, and a focusing means. All the elements are combined together and properly positioned and aligned in a rigid body or housing. Numerous other configurations of the internal components are possible including the addition of temperature compensating means, and various arrangements of optical components.

In operation, the liquid measurand is sandwiched between the measuring surface of a prism and an externally mounted transparent cover. Light incident upon the measuring surface of the prism passes through the exit surface, at an angle relative to the measuring surface. An objective lens focuses this light on an image plane or reticle. The reticle is usually a small piece of glass or other transparent material with an analog scale image etched vertically across its face. Tiny horizontal divisions divide the vertical scale and are representative of some specific unit of measure related to the refractive index of the solution.

Light focused on the image plane creates a shadowline or demarcation, at the critical angle, which separates the field of the reticle into light and dark regions. Very small changes in the refractive index of the liquid under test will create corresponding small vertical movement in the shadowline. It is not necessary to describe in any greater detail the path of the light energy through the optical elements or the formation of the image on the image plane, since it is elucidated in numerous patents and textbooks and is well known to those skilled in the art of refractometry.

A few refractometers with illuminating means have previously been disclosed in U.S. Pat. Nos. 2,601,128 and 4,650,323 and most notably is U.S. Pat. No. 4,890,916. These prior art refractometers have included illuminating means attached to a refractometer body or housing in a hinged sample cover superior to the measuring surface of a prism.

One disadvantage of the prior art refractometers is that the illuminating means is positioned in a hinged sample-cover suspended above the measuring surface. When the power source and electronics are housed in the sample cover, the cover becomes bulky and these elements can in fact impede ambient light passing through the cover, as well as create secondary shadows and/or reflections.

Another disadvantage to the prior art is that the sample cover is prone to damage since it is mounted externally on the refractometer body. Most importantly, the prior art provides for general illumination perpendicular to the plane of the measuring surface instead of at a preferred grazing angle of incidence.

A further disadvantage of prior art is that pressure induced by pressing on the sample cover to actuate the light source can squeeze the liquid sample from between the sample cover and the measuring surface or cause enough mechanical pressure on the prism to actually move the prism with respect to the other optical components causing an erroneous reading. Another disadvantage of this invention is that the amount of space available for mounting a light source and battery limits the size and life of the battery.

Various advantages of the present invention distinguish it from prior art. Because the illumination of the present invention is supplied at either a grazing incidence to the measuring surface or from below the measuring surface, light is incident relative to the prism in the direction necessary to best enhance the measurement of refractive index. Further, since the illumination means is provided in the body or housing of the refractometer it is sturdier and not prone to breakage or damage as in an externally mounted illuminating means.

DISCLOSURE OF THE INVENTION

The present invention concerns an illuminating means for a hand-held critical angle type refractometer having a body housing, a sample cover assembly, a prism assembly and measuring assembly for measuring the composition and density of a substance. An illuminating means for the refractometer in accordance with a preferred embodiment the present invention includes a light source, a power source for operating said light source, and an operating means for selectively activating the light source. The illuminating means is housed in the refractometer body to introduce light at a grazing incidence to a measuring surface of the prism. While a grazing incidence is preferred, other angles of incidence are contemplated by the present invention. The sample cover may be transparent so as to allow ambient light to light the measuring surface when possible.

The illuminating means of the preferred embodiment may be selectively powered, as needed, by a switching means being brought into electrical contact with a power supply, both of which are integral to the instrument. For the purpose of this embodiment the illuminating means consists of an LED providing visible light directly in front of the primary prism, however it is still within the scope of this invention to use other types of illuminating devices.

In another form of the invention, the actual illumination device is located remotely from the prism area and light energy is conducted to the prism area by means of an optical element, light pipe, wave guide, or optical fiber.

In still another form of the invention, the sample cover is comprised of a transparent oxide glass doped with a rare earth ion or alternatively molded from a resin containing a phosphorescent pigment or material. Optical energy from the illuminating means, as well as ambient light, will excite the sample cover causing it to luminesce or phosphoresce, providing visible illumination for the reticle scale lasting for several hours after exposure to light.

In still another embodiment of the present invention, the illuminating means is housed within the body of the instrument and positioned underneath the forward edge of the primary prism providing illumination for the scale.

These and other objects, features and advantages will become clearer from the following description of the preferred embodiment read in connection with the accompanying drawings.

BRIEF DESCRIPTION OF THE DRAWINGS

FIG. 5. is a schematic diagram of elements of the alternative embodiment in FIG. 4;

FIG. 6A is a representations of a reticle image for the hand-held refractometer described in FIG. 2; and FIG. 6B is a representations of a reticle image for the hand-held refractometer described in FIG. 4 and 5.

DETAILED DESCRIPTION OF THE PREFERRED EMBODIMENT

Figure 1:
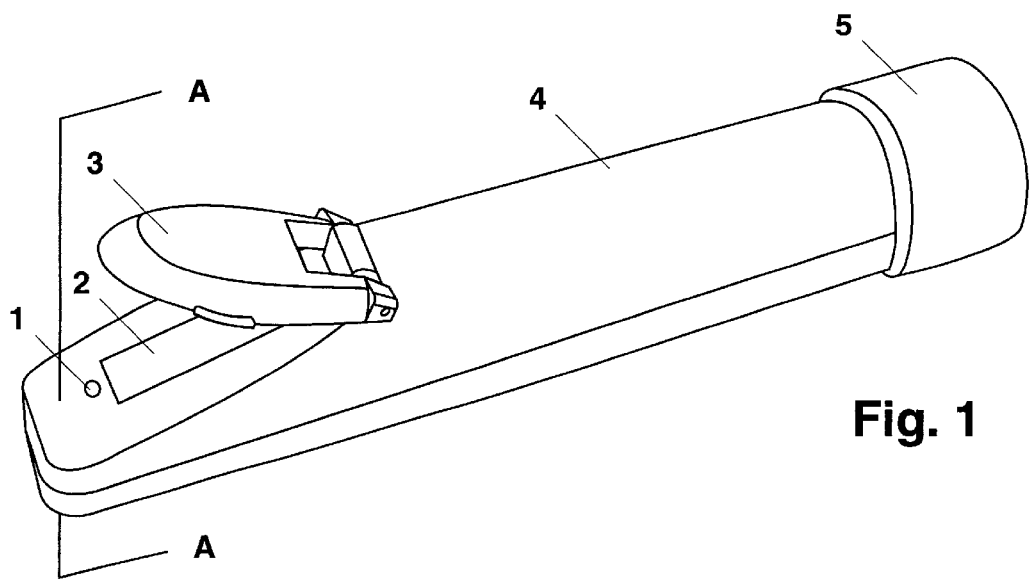
FIG. 1 is a perspective view of a hand-held refractometer with an illuminating means in accordance with the present invention.

As best shown in FIG. 1, a preferred embodiment of the present invention is a hand-held refractometer including a housing 4 which incorporates a light source 1, a primary prism 2, a transparent sample cover 3, and an eyepiece 5.

Figure 2:
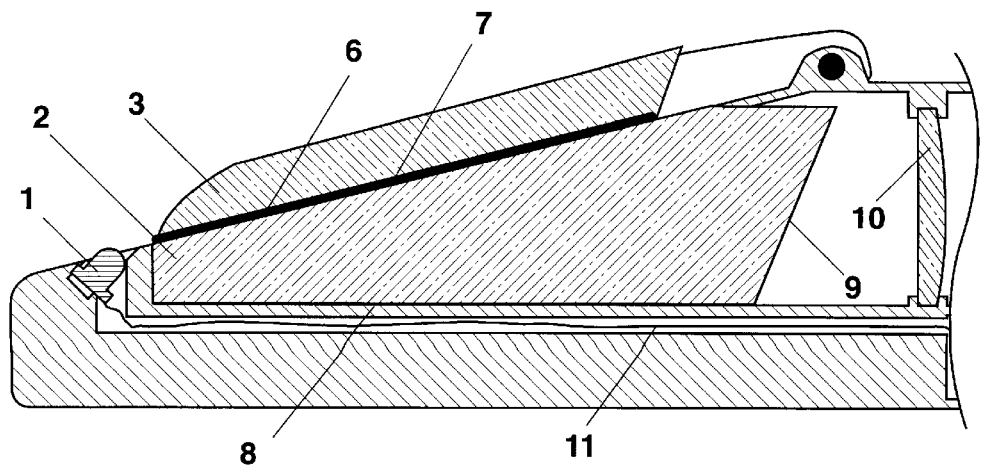
FIG. 2 is an enlarged side view detailed section of the illuminated refractometer taken along the line A—A of FIG. 1.

The operation of the preferred embodiment is best shown in FIG. 2. A liquid sample 6 is sandwiched between a first planar surface 7 of a primary prism 2 and a sample cover 3. Light at grazing incidence to the planar measuring surface 7 passes through the liquid sample 6 and through prism 2. Light exiting through the planar exit surface 9 is imaged by objective lens 10 onto a reticle (see FIG. 6B). Depending on the critical angle of the liquid sample 6 a shadowline will be imaged onto the reticle separating the reticle horizontally into light and dark regions. The reading is taken at the boundary of this separation.

In some instances, there will not be enough ambient light to sufficiently illuminate the scale to take a reading. In such cases, a switching means (not shown) may be activated to supply electrical energy from a power source (not shown) to power the light source 1. Because of the unique positioning of the light source 1 relative to the primary prism 2 and the fluid sample 6, light will be introduced at grazing incidence to planar measuring surface 7. This optical energy will follow the path of light previously described and cause a shadowline to be imaged onto the reticle regardless of the amount of ambient light present outside the instrument.

In another embodiment, the sample cover 6 is comprised of a transparent oxide glass doped with a rare earth ion. Optical energy from the light source 1, which in this particular embodiment emits light in the 800–1000 nm wavelength, as well as ambient light, will excite the sample cover 6 causing it to phosphoresce, providing visible illumination for the reticle scale (not shown). It is also within the scope of this invention to provide light at wavelengths other than 800–1000 nm and for a sample cover 6 to be molded from an optically luminescent material which visibly luminesces, or glows, when stimulated by light. In yet another embodiment, illumination for the reticle scale may be provided by molding the sample cover 6 from a resin containing phosphorescent pigment. Use of a sample cover made of doped oxide glass or resin containing phosfluorescent pigment provides light to illuminate the reticle scale for up to ten hours after exposure to light. In the present invention, reticle illumination may be accomplished even when ambient light is the light source.

Figure 3:
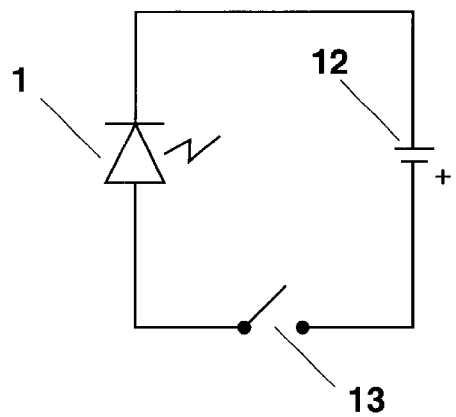
FIG. 3. is a schematic diagram for the electronic components of FIG. 1.
Figure 7:
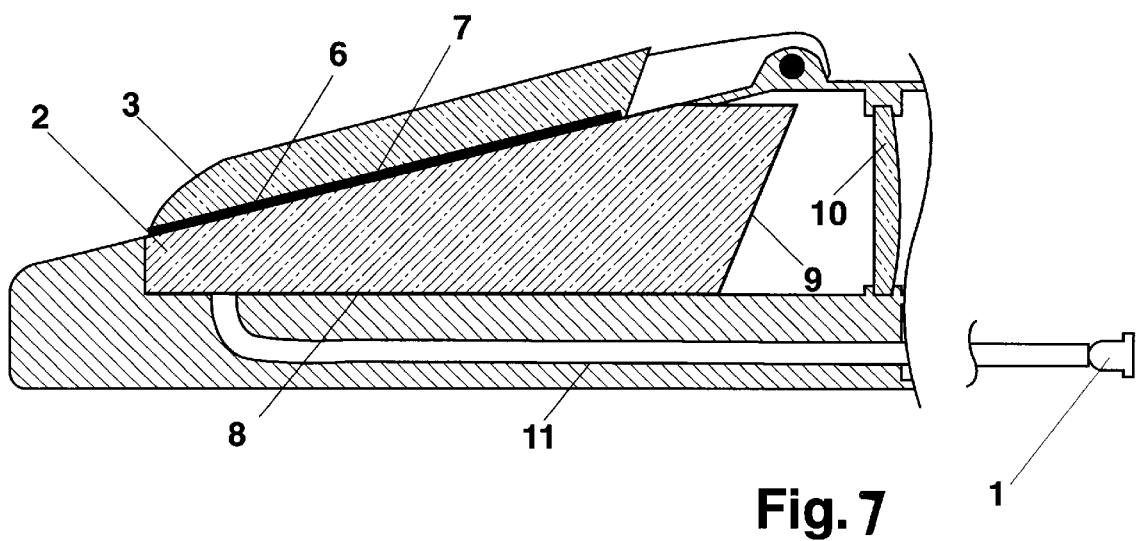
FIG. 7 is an alternative embodiment of the present invention.

Electronic circuitry for operating the illumination system is shown schematically in FIG. 3. It consists of a power source 12, an light source 1, and a switching means 13. In the preferred embodiment the light source consists of a light emitting diode, however, it may also consist of a halogen source, an incandescent source, a neon source, an electroluminescent source, a fluorescent source or any other portable light source alone or in multiple combination with each other. For example, see FIG. 7 which shows a remotely mounted light source.

The aforementioned switching means 13 may consist of a momentary push button, an on/off switch, a potentiometer to vary the intensity of the light passing through the optical system or any other type of switching means that will selectively supply power to the light source 1. The power supply of the preferred embodiment is a coin cell battery, however, any other type of portable power supplies, including photovoltaic cells, is also within the scope of this invention. Various other electronic components, such as resistors, may also be included and are within the scope of this patent.

Figure 4:
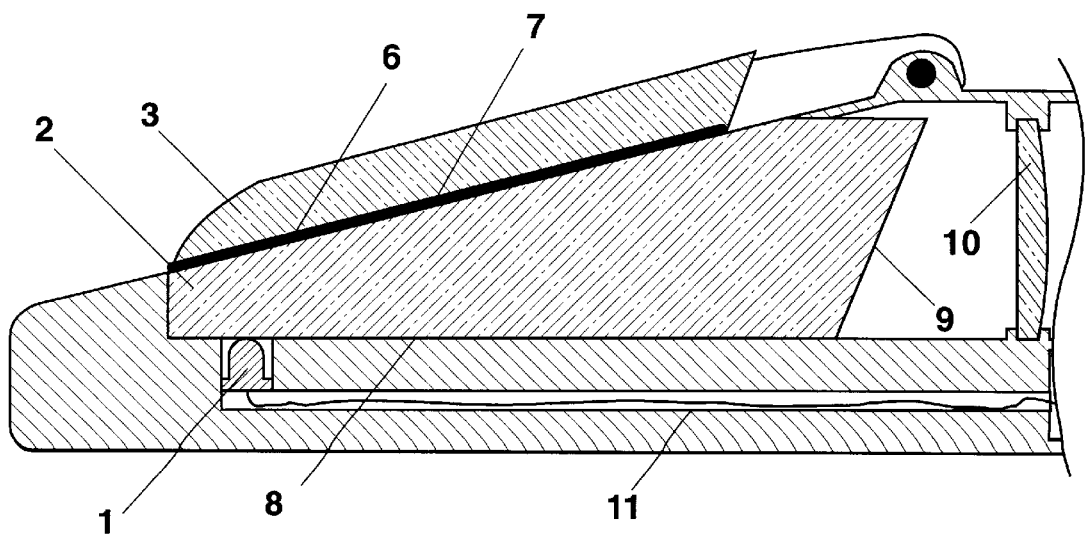
FIG. 4. is an alternative embodiment of the present invention.

In another embodiment, FIG. 4, the light source 1 is located below the primary prism 2 and selectively supplies optical energy through a small transparent aperture in the bottom of the third planar surface 8 of primary prism 2. In this embodiment it is preferable to have the third planar surface 8 coated with an optically opaque coating except in the area of the aperture. In this embodiment it is also preferable that the sample cover 3 be opaque as well, so visible light will not enter through the measuring surface.

Referring now to FIGS. 5 and 6B, all optical energy from the light source 1 that is incident to the inner surface of measuring surface 7 at any angle less than the critical angle 18 will be refracted (transmitted) 20 into the measurand 6 and will cause a dark region 16 to be imaged onto the reticle 14. All light incident on the inner surface of measuring surface 7 at greater than the critical angle 18 will be totally internally reflected 22 and cause an illuminated region 17 to be imaged on the reticle 14. The reading will be taken at the point 18 the boundary between light and dark crosses the graduated scale on the reticle 14. It is important to note that the light and dark fields will be inverted with respect FIG. 6A which shows the shadowline 18 as imaged onto the reticle 14 of a conventional critical-angle refractometer with light incident on the measuring surface 7 from outside the instrument.

Although a preferred embodiment of the invention has been disclosed herein for purposes of illustration, it should be noted that various changes and modifications and substitutions may be incorporated into such an embodiment without departing from the spirit of the invention as claimed below.

We claim:

1. A refractometer having a body housing, a sample cover assembly, a prism assembly and measuring assembly for measuring the composition and density of a substance, said refractometer comprising:
   a) a light source;
   b) a power source for operating said light source;
   c) operating means for selectively activating the light source;
   d) said light source, power source and operating means together defining an illuminator assembly for supporting the light source in a position on or about said prism assembly to illuminate a fluid substance to be measured, wherein said light source is mounted forward of the prismatic element to introduce light at grazing incidence to the measuring surface of said prism;
   e) said light source being housed in the refractometer body and on or about said prism assembly; and
   f) wherein said measuring assembly includes a reticle and an eyepiece for making a quantitative determination of a physical property of a substance directly related to its refractive index.

2. A refractometer having a body housing, a sample cover assembly a prism assembly and measuring assembly for measuring the composition and density of a substance, said refractometer comprising:
   a) a light source;
   b) a power source for operating said light source;
   c) operating means for selectively activating the light source;
   d) said light source, power source and operating means together defining an illuminator assembly for supporting the light source in a position on or about said prism assembly to illuminate a fluid substance to be measured, wherein said light source is remotely located from said prismatic element and light is introduced at grazing incidence to the measuring surface of said prism by way of a light guiding means;
   e) said light source being housed in the refractometer body and on or about said prism assembly; and
   f) wherein said measuring assembly includes a reticle and an eyepiece for making a quantitative determination of a physical property of a substance directly related to its refractive index.

3. A refractometer having a body housing, a sample cover assembly, a prism assembly and measuring assembly for measuring the composition and density of a substance, said refractometer comprising:
   a) a light source;
   b) a power source for operating said light source;
   c) operating means for selectively activating the light source;
   d) said light source, power source and operating means together defining an illuminator assembly for supporting the light source in a position on or about said prism assembly to illuminate a fluid substance to be measured,
   e) said light source being housed in the refractometer body and on or about said prism assembly;
   f) wherein said measuring assembly includes a reticle and an eyepiece for making a quantitative determination of a physical property of a substance directly related to its refractive index; and
   g) wherein said sample cover assembly is comprised of a transparent oxide glass doped with a rare earth ion and said light source introduces the optical energy required to excite said sample cover causing it to phosphoresce and provide visible illumination for a reticle scale.

4. A refractometer having a body housing, a sample cover assembly, a prism assembly and measuring assembly for measuring the composition and density of a substance, said refractometer comprising:
   a) a light source;
   b) a power source for operating said light source;
   c) operating means for selectively activating the light source;
   d) said light source, power source and operating means together defining an illuminator assembly for supporting the light source in a position on or about said prism assembly to illuminate a fluid substance to be measured,
   e) said light source being housed in the refractometer body and on or about said prism assembly;
   f) wherein said measuring assembly includes a reticle and an eyepiece for making a quantitative determination of a physical property of a substance directly related to its refractive index; and
   g) wherein said sample cover assembly is comprised of a resin containing phosphorescent pigment and said light source introduces the optical energy required to excite said sample cover causing it to phosphoresce and provide visible illumination for said reticle scale.

5. A refractometer having a body housing, a sample cover assembly, a prism assembly and measuring assembly for measuring the composition and density of a substance, said refractometer comprising:
   a) a light source;
   b) a battery for operating said light source;
   c) operating means for selectively activating the light source;
   d) said light source, power source and operating means together defining an illuminator assembly for supporting the light source in a position on or about said prism assembly to illuminate a fluid substance to be measured; and
   e) said light source being housed in the refractometer body forward of said prism assembly and introducing light at a grazing incidence to a measuring surface of said prism.

6. A refractometer according to claim 5, wherein said light source is remotely located from the prismatic element and light is introduced at angle beneath the measuring surface of said prism by way of a light guiding means.

7. A refractometer according to claim 5 wherein said sample cover assembly is comprised of a transparent oxide glass doped with a rare earth ion and said light source introduces the optical energy required to excite said sample cover causing it to phosphoresce and provide visible illumination for a reticle scale.

8. A refractometer according to claim 5 wherein said sample cover assembly is comprised of a resin containing phosphorescent pigment and said light source introduces the optical energy required to excite said sample cover causing it to phosphoresce and provide visible illumination for a reticle scale.

9. A refractometer having a body housing, a sample cover assembly, a prism assembly and measuring assembly for measuring the composition and density of a substance, said refractometer comprising:

a) a light source;
   b) a battery for operating said light source;
   c) operating means for selectively activating the light source;
   d) said light source, power source and operating means together defining an illuminator assembly for supporting the light source in a position on or about said prism assembly to illuminate a fluid substance to be measured; and
   e) said light source being housed in the refractometer body beneath said prism assembly and wherein said light source is remotely located from the prismatic element and light is introduced at an angle beneath the measuring surface of said prism by way of a light guiding means.

10. A refractometer according to claim 9 wherein said sample cover assembly is comprised of a transparent oxide glass doped with a rare earth ion and said light source introduces the optical energy required to excite said sample cover causing it to phosphoresce and provide visible illumination for a reticle scale.

11. A refractometer according to claim 9 wherein said sample cover assembly is comprised of a resin containing phosphorescent pigment and said light source introduces the optical energy required to excite said sample cover causing it to phosphoresce and provide visible illumination for a reticle scale.

12. An illuminator for use in a refractometer having a body housing, a sample cover assembly, a prism assembly, a reticle, and measuring assembly for measuring the composition and density of a substance, wherein said sample cover assembly comprises a light reactive material for illuminating said reticle.

13. An illuminator according to claim 12 wherein said light reactive material is oxide glass doped with a rare earth ion.

14. An illuminator according to claim 12 wherein said light reactive material is resin containing phosphorescent pigment.

\* \* \* \* \*